United States Patent [19]

McGregor

[11] 4,308,181

[45] Dec. 29, 1981

[54] POLYPEPTIDE COMPOSITIONS

[75] Inventor: William H. McGregor, Malvern, Pa.

[73] Assignee: American Home Products Corporation, New York, N.Y.

[21] Appl. No.: 213,965

[22] Filed: Dec. 8, 1980

[51] Int. Cl.³ .................... C08L 37/00; C07C 103/52
[52] U.S. Cl. ................................ 260/8; 260/112.5 R
[58] Field of Search ............................ 260/8, 112.5 R

[56] References Cited

U.S. PATENT DOCUMENTS 4,171,299 10/1979 Hamburger .................. 260/112.5 R Primary Examiner—Delbert R. Phillips Attorney, Agent, or Firm—George Tarnowski

[57] ABSTRACT

There are disclosed tetrapeptides having the formula:

$R_1$-Ser-His-Leu-$R_2$ wherein $R_1$ is N-lower alkanoyl or N-lower alkanoylGly; $R_2$ is $NH_2$ or Val-$NH_2$; the fully protected peptide-resin intermediates thereof and pharmaceutically acceptable salts thereof. These tetrapeptides have the capability of inducing the proliferation of T-cell populations and thus are useful in a number of therapeutic areas.

5 Claims, No Drawings

POLYPEPTIDE COMPOSITIONS

BACKGROUND OF THE INVENTION

Recent research has established that the insulin molecule is capable of inducing T cell proliferation in laboratory animals. The T-cells have immunological specificity and are involved in the cell-mediated immune responses, such as graft responses, response to viral infections, response to neoplasms and so forth. The body's response to antigenic material, such as for example in response to bacterial attack, is the province of antibody secreting cells, called B-cells, which are derived from bone marrow stem cells, but which are not differentiated in the thymus. The antibody response to an antigen, in many cases, requires the presence of appropriate T-cells, so that T-cells are necessary for the body's immune system to make not only cellular immunity responses, but also humoral antibody response.

Current interest in control of the immune response to chemically well-defined natural and synthetic polypeptides has resulted in significant new research discoveries. A particularly interesting finding is that insulin has a profound influence on the overall capacity of an animal to mount a thymus-dependent immune response to the molecule as a whole.

Thus, Snow et al in *The Journal of Immunology*, volume 124, number 2, pages 739–744, 1980, have demonstrated that the presence of insulin enhanced the Concanavalin A (Con A) reactivity of murine lymphocytes. Once the cells were activated by short-term exposure to Con A, insulin was capable of replacing Con A for the continued stimulation of the cells. This was true both for lymphocyte proliferation and for the generation of nonspecific cytotoxic T lymphoctye. An important aspect of the postulated theory for the proliferative activity observed is the expression of surface insulin receptors on the cells.

Rosenthal et al in *Advances in Experimental Medicine and Biology*, volume 98, pages 447–458, 1980, have demonstrated that definite regions of the insulin molecule are responsible for the capacity of various subjects, such as mice, guinea pigs and man, to mount a thymus-dependent response to the overall insulin molecule. The thymus-dependent responses comprise activation of T cell function and generation of specific T help and suppression. Rosenthal et al further postulate that the immune response to insulin is genetically determined, with the responsible gene functioning by making an intramolecular selection of discrete regions within the insulin molecule for recognition by the T cell at its insulin receptor site.

Thus, the evidence is strong that the insulin molecule or portions thereof, is capable of affecting the proliferation of T cells as well as affecting T cell subpopulatives, such as T suppressor cells. The T cell subpopulations of suppressor and helper T cells have been implicated in a number of immune response manifestations. Thus, the impairment of suppressor T cell activity is now believed to be a major factor in such autoimmune connective tissue disease as systemic lupus erythematosus. Moreover, in the latter case, as well as in probable impaired immune system responses such as rheumatoid arthritis, it is believed the helper T cells exacerbate the condition.

Also, the theory has been advanced that T suppressor cell hypofunctioning, resulting in inadequate T-B cell cooperation in the immune response, with continuous B cell stimulation and subsequent antibody production may be the cause of the production of antigen-antibody complexes which are the causative agents of renal and inflammatory processes in arthritis and autoimmune diseases.

Thus, it is now apparent that a number of lymphopoietic disorders are undoubtedly associated with abnormalities of T cell and especially suppressor cell function. The loss of suppressor function is at least an early event in certain immune response diseases and is a disease-perpetuating mechanism in others. The loss of suppressor function probably leads to excessive lymphoid cell proliferation and may significantly contribute to lympho-proliferative disorders. The conditions created thereby may be exacerbated by helper T cells.

Compounds capable of inducing T cell proliferation are therefore useful in the therapeutical treatment of various disorders of the immune response.

The present invention relates to short peptide sequences which are synthetic fragment analogs of insulin B chain 8–12 and have been found to exhibit the T cell proliferation inducing properties of the insulin molecule.

DESCRIPTION OF THE INVENTION

In accordance with this invention, there is provided a novel group of tetrapeptides having the structural formula:

$R_1$-Ser-His-Leu-$R_2$ wherein $R_1$ is N-loweralkanoyl or N-loweralkanoylGly and $R_2$ is $NH_2$ or Val-$NH_2$, the fully protected peptide-resin intermediate thereof, and the pharmaceutically acceptable salts thereof.

In the depicted formula and throughout the specification and claims, where the chirality of an amino acid is not indicated or otherwise stated, it is understood to be of the L-series. The term lower alkanoyl refers to alkanoyl groups having a carbon atom content of 2-6 carbons.

The fully protected tetrapeptide-resin intermediates, which comprise an additional aspect of the invention, may be depicted as follows:

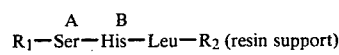

$R_1$—Ser—His—Leu—$R_2$ (resin support)
        A   B wherein $R_1$ and $R_2$ are as defined hereinbefore; and A and B are protecting groups which are hereinafter described. The intermediates comprise the fully protected polypeptide bound to a benzhydrylamine polystyrene resin support employed in the solid phase synthesis of the polypeptides.

The pharmaceutically acceptable salts of the compounds of the invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic, ascorbic and the like.

The peptides of the invention are able to induce the proliferation of T-cell populations, thereby affecting T-cell development. These effects are observable with concentrations as low as 1–100 ng/ml., making these compounds useful in the therapeutical treatment of a number of disorders of the immune response. Because the compounds stimulate certain of the thymic functions, they have application in various thymic function and immunity areas. Thus, the compounds can help to restore immune function and augment specific lymphocyte functions in children with hypothymic function and in adults with a variety of T-cell disorders, including cancer, and autoimmune diseases. The polypeptides will increase or assist in therapeutic stimulation of cellular immunity and thereby become useful in the treatment of diseases involving chronic infection in vivo, such as fungal or mycoplasma infection, tuberculosis, leprosy, acute and chronic viral infections, and the like. Further, the compounds are useful in areas involving immunity deficiencies such as DiGeorge Syndrome, and in treating immunosuppressed cancer patients. The compounds may also be of therapeutic value in certain autoimmune diseases, such as systemic lupus erythematosus.

The peptides are highly active in very low concentrations ranging from 1 nanogram per ml. up to 100 nanograms per ml. The carrier for the compounds may be any of the well known carriers for this purpose including normal saline solution, preferably with a protein diluent such as bovine serum albumin to prevent adsorptive losses to glassware at these low concentrations.

The polypeptides are produced by the well known solid phase method as described by Stewart et al., *Solid Phase Peptide Synthesis*, Freeman and Co., San Francisco, 1969. As applied to some of the compounds of this invention, α-amino protected valine is attached to a benzhydrylamine polystyrene resin followed by removal of the α-amino protecting group with trifluoroacetic acid in methylene chloride, trifluoroacetic acid alone or HCl in dioxane. The deprotection is carried out at temperatures between about 0° C. and room temperature. Other standard cleaving reagents and conditions for removal of specific α-amino protecting groups may be used as described in Schroder and Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagent employed is diisopropylcatbodiimide.

After the desired amino acid sequence has been synthesized, the polypeptide is removed from the resin support by treatment with hydrogen fluoride and anisole to obtain the fully deprotected polpeptide. The polypeptide is then purified by one or more purification techniques, including gel filtration, high pressure preparative liquid chromatography and partition chromatography.

The ultimate fully protected, resin bound tetrapeptides of this invention specifically exemplified are t-Boc-O-benzyl-L-seryl-N$^{im}$-tosyl-L-histidyl-L-leucyl-L-valyl benzhydrylamine polystyrene amide; and t-Boc-L-glycyl-O-benzyl-L-seryl-N$^{im}$-tosyl-L-histidyl-L-leucyl benzhydrylamine polystyrene amide.

The protecting groups employed throughout the solid phase synthesis are well known to the art. The α-amino protecting group employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl allyloxycarbonyl, 2,2,3-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

Protection for the hydroxyl group of serine may be with the acetyl, benzoyl, t-butyl or benzyl group. Preferably benzyl is employed to protect the hydroxy group.

Protection of the imidazole nitrogen of histidine may be by tosyl, benzyl, trityl, benzyloxycarbonyl groups, with the tosyl group being preferred.

In selecting a particular side-chain protecting group to be used in the synthesis of the peptides of this invention, the following rules should be followed: (a) the side-chain protecting group must be stable to the reagent and under the reaction conditions selected for removing the α-amino protecting group at each step of the synthesis, (b) the protecting group must retain its protecting properties (i.e. not be split off under coupling conditions), and (c) the side-chain protecting group must be removable upon the completion of the synthesis containing the desired amino acid sequence under reaction conditions that will not alter the peptide chain.

The following examples illustrate the preparation of N-acetylglycyl-L-seryl-L-histidyl-L-leucinamide, acetate; N-acetylseryl-L-histidyl-L-leucyl-L-valinamide; acetate.

EXAMPLE 1 t-Boc-L-glycyl-O-benzyl-L-seryl-N$^{im}$-tosyl-L-histidyl-L-leucyl benzhydrylamine polystyrene amide In a solid phase peptide synthesizer 7 g benzyhydrylamine hydrochloride resin (Bachem) are neutralized twice with 30% triethylamine in methyiene chloride for five minutes each and washed successively with MeCl$_2$ (1 time), DMF (2 times), and coupled with 6.5 gm t-Boc-L-leucine, 4 gm hydroxybenzotriazole, and 4 ml diisopropylcarbodiimide in DMF overnight. After successive washed with DMF (1 time), MeCl$_2$ (2 times), MeOH (1 time) and MeCl$_2$ (3 times), the resin in ninhydrin trace positive and is deprotected with 50% TFA in MeCl$_2$ (containing 0.5% DTE) for 30 minutes and is washed with MeCl$_2$ (1 time), 30% triethylamine in DMF (2 times) and DMF (2 times). It is coupled with 10 gm t-Boc-im-Tos-L-histidine and 4 ml diisopropylcarbodiimide overnight. After successive washing (as previously) the peptidyl-resin is still ninhydrin positive so was recoupled with 10 gm t-Boc-im-Tos-L-histidine and 4 ml diisopropylcarbodiimide over the weekend. After the usual washing, the peptidyl-resin is slightly ninhydrin positive and is deprotected with trifluoroacetic acid as previously for 30 min. and neutralized and washed as described in the previous deprotection step. The resin is coupled with 9 gm t-Boc(O-benzyl)-L-serine and 4 ml diisopropylcarbodiimide as usual overnight. After the usual washings at this step, the peptidylresin is deprotected with trifluoroacetic acid as previously, neutralized, washed as earlier described and coupled with 5 gm t-Boc-glycine and 4 ml diisopropylcarbodiimide overnight as usual. After the usual washing at this step the peptidyl-resin is slightly ninhydrin positive, is deprotected with trifluoroacetic acid 30 min., neutralized and washed as usual at this stage and coupled with 10 gm acetyl imidazole in DMF overnight. After washing as usual the resin is ninhydrin slightly positive was washed with Et$_2$O and dried in vacuo.

EXAMPLE 2

N-acetylglycyl-L-seryl-L-histidyl-L-leucinaminde, acetate

The above peptidyl-resin of Example 1 is deprotected and cleaved with HF in the presence of 8 ml of anisole for 1 hr at 0° C., the HF removed in vacuo and the residue washed 3 times with ethyl ether, dried in a current of nitrogen and triturated with 150 ml of 0.2 N HOAc for five minutes and filtered. The filtrate after lyophylization gives 697 mg of crude AcGly-Ser-His-Leu-NH$_2$.HOAc.

150 mg of the above peptide are chromatographed on Sephadex G-10 using 0.2 N acetic acid as solvent at a flow rate of 15 ml per hour and collecting 1 ml fractions. Fractions 57–64 are combined on the basis of TLC silica gel BAW R$_f$ 0.05 (peptide-chlorine spray) and lyophylized to yield 73 mg of this title compound.

Amino acid analysis of the product gave the following:

NH$_3$ 1.15; Ser 0.96; Gly 1.22; Leu 1.0; His 0.97.

EXAMPLE 3 t-Boc-O-benzyl-L-seryl-N$^{im}$-tosyl-L-histidyl-L-leucyl-L-valyl benzhydrylamine polystyrene amide In a solid phase peptide synthesizer 7 gm benzhydrylamine hydrochloride resin (Bachem) are neutralized twice with 30% triethylamine in methylene chloride for 5 min. each and washed successively with MeCl$_2$ (1 time), DMF (2 times) and coupled with 6 gm t-Boc-L-valine, 4 gm hydroxybenzotriazole and 4 ml diisopropylcarbodiimide over the weekend. After successive washing with DMF (1 time), MeCl$_2$ (2 times), MeOH (1 time) and MeCl$_2$ (3 times) the resin is ninhydrin trace positive and is deprotected 30 min. with 50% trifluoroacetic acid in methylene chloride (containing 0.5% DTE) washed with MeCl$_2$ (1 time, 30% triethylamine in DMF (2 times) and DMF (2 times). It is coupled with 6.5 gm t-Boc-L-leucine, 4 gm hydroxybenzotriazole and 4 ml diisopropylcarbodiimide for 48 hours. After being washed as usual at this step, the peptidyl-resin is ninhydrin trace positive and is deprotected with trifluoroacetic acid as previously described for this step, washed and neutralized as usual and coupled with 10 gm t-Boc-im-tosyl-L-histidine and 4 ml diisopropylcarbodiimide in DMF over the weekend. After the usual washing at this step the peptidyl-resin is still ninhydrin positive and is recoupled with 10 gm t-Boc-im-Tosyl-L-histidine and 4 ml diisopropylcarbodiimide in DMF overnight. After the usual washing at this step the peptidyl resin is slightly ninhydrin positive, is deprotected with trifluoroacetic acid as usual, washed and neutralized as usual at this stage and coupled with 9 gm t-Boc-(O-benzyl)-L-serine, and 4 ml diisopropylcarbodiimide in DMF over the weekend. The peptidyl-resin is still ninhydrin positive at this stage after washing and is further recoupled with 9 gm t-Boc-(O-benzyl)-L-serine and 4 ml diisopropylcarbodiimide overnight in DMF. The peptidyl-resin after washing as usual at this point is ninhydrin slightly positive, is deprotected with TFA, washed and neutralized as usual and coupled with 10 gm acetyl imidazole in DMF overnight. After the usual washing at this stage the peptidyl resin is ninhydrin positive and is recoupled with 10 gm acetylimidazole in DMF overnight. The resin is slightly ninhydrin positive after washing as usual. It is then washed with Et$_2$O and dried in vacuo.

EXAMPLE 4

N-acetylseryl-L-histidyl-L-leucyl-L-valinamide, acetate

The peptidyl-resin of Example 3 is cleaved and deprotected simultaneously with HF in the presence of 8 ml of anisole for 1 hr at 0° C. the HF removed in vacuo and the residue washed 3 times with ethyl ether, dried in a current of nitrogen and triturated with 150 ml of 0.2 N acetic acid for five minutes and filtered. The filtrate after lyophylization gives 733 mg of crude Ac-Ser-His-Leu-Val-NH$_2$. HOAc.

150 mg of the above crude peptide are chromatographed on a 1.5×100 cm column of Sephadex G-10 using 0.2 N acetic acid as elutant at a flow rate of 15 ml per hour. and collecting 1 ml fractions. Fractions 61–67 are combined on the basis of TLC silica gel BAW R$_f$ 0.08 (peptide-chlorine spray) and lyophylized to yield 73 mg of the title compound.

Amino acid analysis of the product gave the following:

Ser 1.02; His 1.05; Leu 1.00; Val 1.01; NH$_3$ 1.21.

EXAMPLE 5

The activity of the compounds of the Examples is determined according to the following procedure:

T lymphocytes are isolated from spleens of male CBA/J or NZB mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% CO$_2$, for 45 minutes. The non-adherant T lymphocytes are then eluted from the column, counted, and adjusted to 20×10$^6$ cells/ml. 50 μl. of cells are cultured (37° C., 95% air, 5% CO$_2$) with compound, for 48 hours before addition of 0.5 μCi. of 3H-thymidine for the last 16 hours of culture. The total volume of the culture system is 200 μ l. The cells are then harvested on a multiple automatic sample harvester (MashII), the glass fiber filter disks placed in 10 ml. of xylene base scintillation fluid, and counted for 1 minute in a liquid scintillation counter. Results are reported as CPM+SE. Comparisons are made between counts obtained with control cultures and cultures containing compound and a determination made as to whether the compounds are active at the dosage tested. The findings are summarized in Table 1.

TABLE 1

| Compound | Concentration (ng/culture) | N* | H-Thymidine Uptake CPM + S.E. | p |
|---|---|---|---|---|
| Ac—Ser—His—Leu—Val—$NH_2$ | 0 | 10 | 9,876 ± 951 | |
| | 1.5 | 5 | 30,925 ± 3256 | <0.01 |
| | 6.0 | 5 | 26,741 ± 3049 | <0.01 |
| | 25 | 5 | 28,206 ± 2233 | <0.01 |
| | 100 | 5 | 20,758 ± 3027 | <0.02 |
| Ac—Ser—His—Leu—Val—$NH_2$ | 0 | 8 | 19,275 ± 1298 | |
| | 0.75 | 5 | 26,137 ± 6158 | N.S. |
| | 1.5 | 4 | 32,646 ± 2284 | <0.01 |
| | 6.0 | 2 | 30,425 ± 8896 | <0.1 |
| | 25 | 5 | 32,278 ± 5373 | <0.01 |
| Ac—Gly—Ser—His—Leu—$NH_2$ | 0 | 10 | 9,876 ± 951 | |
| | 1.5 | 5 | 15,028 ± 1178 | <0.02 |
| | 6.0 | 5 | 19,423 ± 1031 | <0.01 |
| | 25 | 5 | 19,433 ± 3092 | <0.02 |
| | 100 | 5 | 20,409 ± 4081 | <0.05 |
| Ac—Gly—Ser—His—Leu—$NH_2$ | 0 | 10 | 19,275 ± 1298 | |
| | 0.75 | 4 | 41,019 ± 6047 | <0.01 |
| | 1.5 | 3 | 48,033 ± 5499 | <0.02 |
| | 6 | 4 | 38,254 ± 7188 | >0.05 |

*= N equals number of animals

The results show that the peptides of the invention have marked activity in stimulating the proliferation of T-cells at very low concentration levels.

What is claimed is:

1. A tetrapeptide having the following formula:

$R_1$-Ser-His-Leu-$R_2$ wherein $R_1$ is N-lower alkanoyl or N-lower alkanoyGly; $R_2$ is $NH_2$ or Val-$NH_2$; the fully protected peptide-resin intermediates thereof, and pharmaceutically acceptable salts thereof.

2. The compound of claim 1, which is acetyl-Gly-Ser-His-Leu-$NH_2$ or a pharmaceutically acceptable salt thereof.

3. The compound of claim 1, which is acetyl-Ser-His-Leu-Val-$NH_2$ or a pharmaceutically acceptable salt thereof.

4. A compound of the formula:

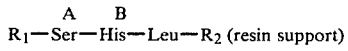

wherein $R_1$ is N-lower alkanoyl or N-lower alkanoylGly; $R_2$ is $NH_2$ or Val-$NH_2$; A is a hydroxy protecting group; and B is an imidazole nitrogen protecting group.

5. The compound of claim 4, having the formula:

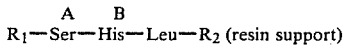

wherein A is benzyl; and B is tosyl.

* * * * *